(12) United States Patent
Wolcott et al.

(10) Patent No.: US 7,767,467 B1
(45) Date of Patent: Aug. 3, 2010

(54) COAXIAL TUBULAR SEQUESTERING DEVICE FOR MICRO SPHERES AND CELLS

(75) Inventors: Duane K. Wolcott, Fox Island, WA (US); Graham D. Marshall, Fox Island, WA (US)

(73) Assignee: Global FIA, Inc., Fox Island, WA (US)

( * ) Notice: Subject to any disclaimer, the term of this patent is extended or adjusted under 35 U.S.C. 154(b) by 0 days.

(21) Appl. No.: 12/622,420

(22) Filed: Nov. 19, 2009

Related U.S. Application Data

(62) Division of application No. 11/308,207, filed on Mar. 12, 2006, now Pat. No. 7,625,762.

(60) Provisional application No. 60/594,134, filed on Mar. 14, 2005.

(51) Int. Cl.
 *G01N 1/18* (2006.01)
(52) U.S. Cl. .................. 436/178; 436/63; 436/174; 436/175; 436/177; 422/101; 422/103; 210/634; 210/644; 210/645; 210/651
(58) Field of Classification Search .................. 436/53, 436/63, 174, 175, 177, 178; 422/68.1, 99, 422/101, 103; 435/4, 29; 210/634, 644, 210/645, 650, 651
See application file for complete search history.

(56) References Cited

U.S. PATENT DOCUMENTS 6,499,362 B1 * 12/2002 Wolcott .................. 73/863.24
6,613,579 B2 * 9/2003 Wolcott .................. 436/178
7,625,762 B1 * 12/2009 Wolcott et al. .............. 436/178

OTHER PUBLICATIONS

Hindson et al. Analytical Chemistry, vol. 76, 2004, pp. 3492-3497.*
Marshall et al. Analytica Chimica Acta, vol. 499, 2003, pp. 29-40.*

* cited by examiner

*Primary Examiner*—Maureen M Wallenhorst
(74) *Attorney, Agent, or Firm*—Reginald F. Roberts, Jr.

(57) ABSTRACT

A device for the separation of small particles or cells from a fluid suspension of the same is described. The device includes a coaxial tubular design in which the inner tube is a micro porous tube that allows the passage of liquids and certain particulates up to a certain size cut-off, and the outer tube allows for the collection of passed fluids. Inlet and outlet ports allow the introduction and flushing of components of interest. Embodiments of the device can be used for the separation of blood components, the sequestering of micro spheres used in micro-sphere-based immuno assay, and sample filtration. Other applications are not precluded. Another field of application for this device is in the separation of plasma from red blood cells. The red blood cells will not pass through the membrane due to their size, but plasma will.

2 Claims, 3 Drawing Sheets

COAXIAL TUBULAR SEQUESTERING DEVICE FOR MICRO SPHERES AND CELLS

CROSS-REFERENCES TO RELATED APPLICATIONS

This application is a division of non-provisional application Ser. No. 11/308,207, filed Mar. 12, 2006 and now U.S. Pat. No. 7,625,762, which is based on provisional Application No. 60/594,134, filed Mar. 14, 2005.

BACKGROUND OF THE INVENTION

The present invention relates to micro spheres. More specifically, the invention relates to sequestering of micro spheres.

Micro spheres are used extensively to capture analytics of interest for various selective assays. For example, micro-sphere-based immuno-assay allows a means of conducting the determination of multiple analytes simultaneously in a single reaction vessel. Molecular reactions take place on the surface of tiny spheres called micro spheres or beads. For each reaction, target molecules are selectively attached to the surface of internally color-coded micro spheres. The assigned color code identifies the reaction throughout the test. The concentration of target molecules is measured using a second kind of molecule called a reporter, which attaches to the target molecule in a sandwich-type reaction.

Early attempts at developing a suitable sequestering cell suffered because of a large pressure drop across the bead barrier. Either the surface area of a porous membrane was too small or where a gap of ca 3 micrometers (μm) was machined, the length of the bead barrier was too short and gave rise to a large back pressure in the sequestering cell. This problem is remedied by the present invention.

SUMMARY OF THE INVENTION

The present invention, in a first aspect, provides a tubular sequestering device for micro spheres, the tubular sequestering device comprising:

a porous tube having an internal volume of from about five to about nine microliters, and pores having a pore size with an appropriate dimension to prevent passage of the micro spheres but allow passage of a liquid, for retaining the micro spheres within the tube while enabling a liquid carrier in which the micro spheres are suspended to pass through the pores of the tube.

In a second aspect, the invention provides a sequestering device for micro spheres, the sequestering device comprising:

first and second passageways for a liquid carrier or for a suspension of the micro spheres in the liquid carrier; and a planar porous disk, disposed between and fluidly connected to the first and second passageways, the porous disk including pores having a pore size with an appropriate dimension to prevent passage of the micro spheres but allow passage of a liquid, for retaining the micro spheres within the disk while enabling the liquid carrier in which the micro spheres are suspended to pass through the pores of the porous disk.

In a third aspect, the invention provides a method for sequestering micro spheres, the method comprising:

using a porous membrane having a pore size with an appropriate dimension for retaining micro spheres suspended in a liquid carrier while passing the liquid carrier through the porous membrane.

In a fourth aspect, the invention provides a method for sequestering micro spheres, the method comprising the steps of:

a. aspirating, with a pump, a suspension of the micro spheres in a liquid carrier;
b. using a holding coil to hold the liquid carrier or a suspension of the micro spheres in the liquid carrier;
c. loading the holding coil with the suspension of the micro spheres, and with additional liquid carrier for washing the micro spheres and for rinsing the holding coil;
d. providing a porous tube having pores with a pore size of an appropriate dimension, for retaining the micro spheres within the porous tube while enabling the liquid carrier in which the micro spheres are suspended to pass through the pores of the tube;
e. disposing the porous tube in a shell configuration to form a sequestering cell equipped with an inlet, an outlet, a waste port, and a flush port;
f. with the waste port open and the flush port and outlet closed, transporting the suspension of the micro spheres to the porous tube through the inlet to the sequestering cell, for retaining the micro spheres in the porous tube while passing the liquid carrier through the pores of the tube;
g. washing the retained micro spheres by flowing the liquid carrier over the retained micro spheres through the inlet to the sequestering cell to the waste port of the sequestering cell;
h. with the waste port and inlet closed and the flush port and outlet open, dislodging the micro spheres from inner surface of the porous tube;
i. with the waste port and flush port closed and the inlet and outlet open, withdrawing a suspension of the washed micro spheres in the liquid carrier from the porous tube;
j. transporting the suspension of the washed micro spheres to a flow cytometer;
k. rinsing the holding coil with the liquid carrier; and
l. preparing to repeat steps a through k by dispensing liquid carrier and a bracketing air bubble to the outlet of the sequestering cell.

DETAILED DESCRIPTION OF THE INVENTION

Figure 1:
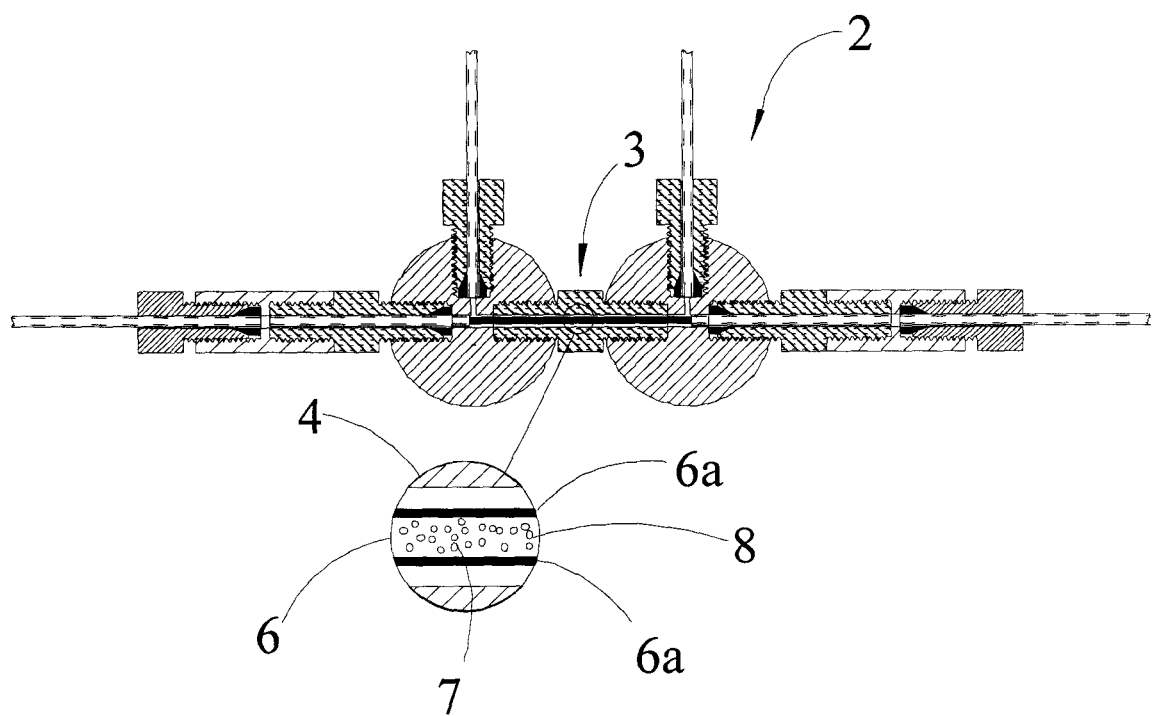
FIG. 1 is a schematic representation of a first and preferred embodiment of a device for sequestering micro spheres, made in accordance with the principles of the present invention.

More specifically, reference is made to FIG. 1, in which is shown a preferred embodiment of a coaxial tubular sequestering device, made in accordance with the principles of the present invention, and generally designated by the numeral 2.

The coaxial tubular sequestering device 2 comprises a sequestering cell 3 which includes an outer shell 4 and an inner porous tube 6 coaxially disposed in the outer shell 4. A plurality of micro spheres 8 suspended in a liquid carrier 7 are disposed within the inner porous tube 6. The coaxial disposition of the porous tube 6 within the outer shell 4 minimizes the internal volume of the porous tube 6 while allowing adequate surface area to avoid excessive pressure drop across the membranous wall 6a as the liquid carrier 7 flows through the membranous wall 6a of the porous tube 6.

The internal volume of the porous tube 6 is small, typically from about five to about nine micro liters, and is preferably about seven micro liters. The pore size of the porous tube 6 is sized to trap the micro spheres 8 while allowing the passage of the liquid carrier 7. The micro spheres 8 should be larger, preferably about ten times larger, than the pores, and they should not be so small or so numerous as to cause excessive back pressure in the sequestering device 2. The mean internal diameter of the porous tube 6 is sized to be compatible with the rest of a fluid-handling manifold, is typically from about five hundred to about seven hundred micrometers, and is preferably about six hundred micrometers. The thickness of the wall 6a of the porous tube 6 is from about one hundred to about three hundred micrometers, and is preferably about two hundred micrometers. The diameter of the micro spheres is typically from about five to about six micrometers. With these typical dimensions, smaller reagent and wash volumes become feasible.

Figure 2A:
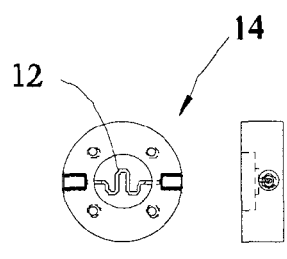
FIGS. 2A, 2B, and 2C are schematic representations of a second embodiment of a device for sequestering micro spheres, made in accordance with the principles of the present invention.
Figure 2B:
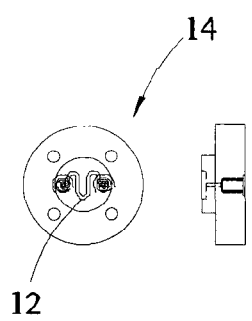
Figure 2C:
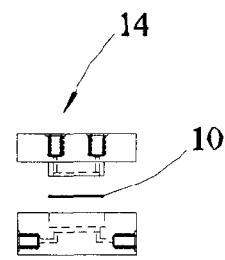

While the tubular arrangement shown in FIG. 1 is believed to be the most efficient, other geometries are also feasible. One such arrangement is shown in FIGS. 2A-2C, in which is shown a second embodiment of a sequestering device, made in accordance with the principles of the present invention, and generally designated by the numeral 14. The sequestering device 14 comprises a planar porous disk or membrane 10 sandwiched between two serpentine passageways 12. The pore size of the porous disk 10 is sized to trap micro spheres while allowing the passage of liquid carrier. The micro spheres 8 should be larger, preferably about ten times larger, than the pores, and they should not be so small or so numerous as to cause excessive back pressure in the sequestering device 2. In a typical application the pore size is from about one-tenth to about three-tenths micrometers, and is preferably about two-tenths of a micrometer.

Typically, the porous tube 6 and the porous disk 10 are made of porous polypropylene. Other suitable materials include porous polyethylene, porous polytetrafluoroethylene, Anapore® filter disks, Nuclepore® filter disks, as well as a wide range of tubular and planar filtration media.

Figure 3:
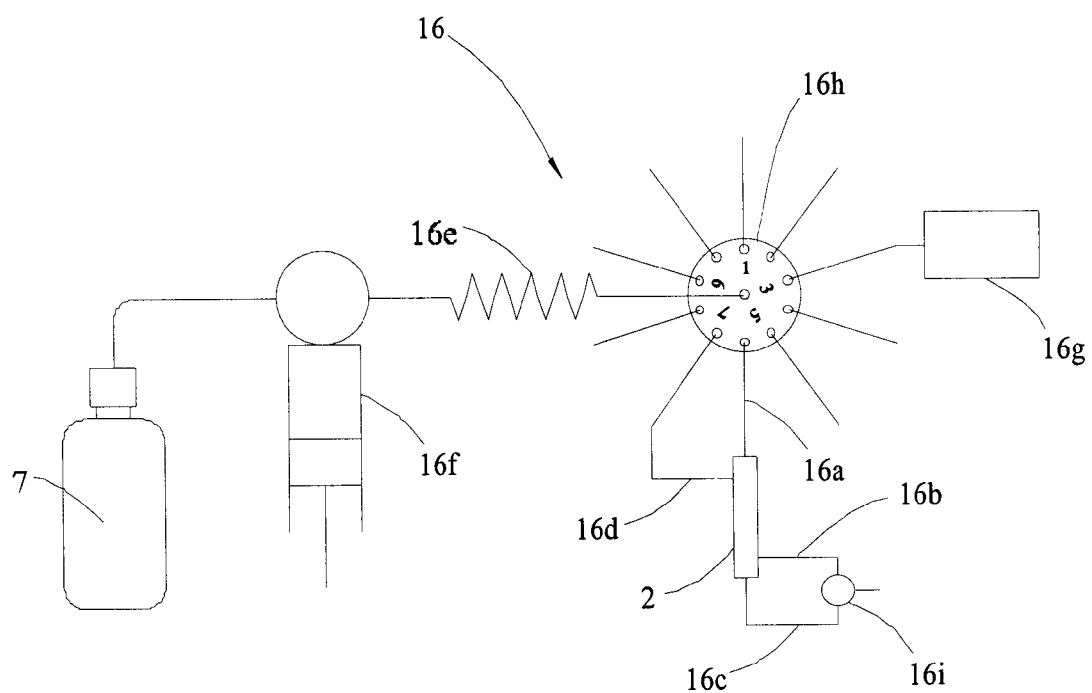
FIG. 3 is a schematic representation of a fluidics manifold, made in accordance with the principles of the present invention.

Reference is now made to FIG. 3, in which is shown a fluidics manifold, made in accordance with the principles of the present invention, and generally designated by the numeral 16. The fluidics manifold 16 is programmed to electronically and automatically control the operation of the coaxial tubular sequestering device 2. The fluidics manifold 16 comprises a bidirectional pump 16f, a holding coil 16e, a first multi-port selection valve 16h, a second multi-port selection valve 16i, an inlet 16a to the sequestering cell 3, a waste port 16b for the sequestering cell 3, a flush port 16d for the sequestering cell 3, an outlet 16c to the sequestering cell 3, and a flow cytometer 16g. The pump 16f aspirates a suspension of the micro spheres 8 in the liquid carrier 7. The holding coil 16e is used to hold the liquid carrier 7 or a suspension of the micro spheres 8 in the liquid carrier 7. The selection valve 16h is fluidly connected to the pump 16f via the holding coil 16e, and to the inlet 16a and the flush port 16d of the sequestering cell 3. The selection valve 16i is fluidly connected to the outlet 16c and the waste port 16b of the sequestering cell 3.

To perform a test, the color-coded micro spheres 8, reporter molecules, and sample are drawn into the holding coil 16e, where they are combined. This mixture is then dispensed to the porous tube 6, with the outlet port 16c and the flush port 16d closed. The liquid carrier 7 passes through the porous tube 6 and to waste via the waste port 16b. The micro spheres 8 are retained on the surface of the porous tube 6a. Further reagent and wash solutions may subsequently be pumped over the micro spheres 8 and to waste. To release the micro spheres 8, a small volume of the liquid carrier 7 is pumped via the flush port 16d while the outlet port 16c is open, and the waste port 16b and inlet 16a are closed. In the next step, the micro spheres 8 are drawn back to the holding coil 16e via the inlet 16a, with the outlet 16c open and the flush port 16d and waste port 16b closed. The micro spheres 8 are then injected into an instrument 16g that uses micro fluidics to align the micro spheres in single file where lasers illuminate the colors inside and on the surface of each micro sphere. Next, advanced optics capture the color signals. Finally, digital signal processing translates the signals into real-time, quantitative data for each reaction. Further automation of the sample handling can be achieved by using an automated fluid handling device to contact the color-coded micro spheres 8, reporter molecules, and sample. To do this, it is convenient to be able to sequester the micro spheres 8 in a cell at a suitable location in the fluid manifold 16, and then wash various reagents, samples, and wash solutions over the micro spheres 8. The present invention describes an apparatus that fulfills the requirements of such a sequestering cell.

A fundamental design principle for the handling of micro spheres 8 in the fluidics manifold 16 is to minimize micro-sphere manipulations by bringing the reagents, samples, and wash solution to the micro spheres 8 rather than devising complicated micro-sphere transfer sequences. Our experience is that micro-sphere manipulation should be kept to a minimum, as micro spheres are easily lost when moving them around in narrow-bore tubing.

The sequestering device should allow for the sequestering of micro spheres but allow the passage of liquid. Devices to accomplish this are not commercially available. The development of such a device is a non-trivial task given the small size of the micro spheres; viz., about five-and-one-half micrometers.

The fluidics manifold 16 is operated according to the following sequence of steps set forth below in Table 1.

TABLE 1

Fluidic Sequence for Coaxial Tubular Design

| Step | Action |
|---|---|
| 1 | Aspirate 75 micro liters (μL) of micro-sphere 8 suspension. |
| 2 | Load 400 μL of liquid carrier 7. |
| 3 | Transport micro-sphere suspension to porous tube 6 through inlet 16a at 10 μL/second, with waste port 16b open, flush port 16d and outlet 16c closed. |
| 4 | Wash volume of liquid carrier 7 over micro spheres 8 through waste port 16b at 10 μL/second. |
| 5 | Dislodge the micro spheres 8 from the surface of the porous tube 6 by dispensing 10 μL of liquid carrier 7 from the flush port 16d through the porous membrane 6a to the outlet 16c. |
| 6 | Withdraw micro-sphere 8 suspension from porous tube 6 at 10 μL/second, with the waste port 16b closed and the outlet 16c open. Outlet line has previously been charged with flush solution and a bracketing bubble (see step 8). |
| 7 | Transport recovered micro spheres 8 to the flow cytometer 16g. |
| 8 | Rinse holding coil 16e with liquid carrier 7. |
| 9 | Prepare inner porous tube 6 for next run by dispensing 100 μL of liquid carrier 7, preceded by a 25 μL air bubble to the outlet 16c. |

Break-through tests indicate that two-tenths micrometer porous tubing is able to sequester the micro spheres 8. The size of the pores should preferably be much smaller than the diameter of the micro spheres 8, to prevent the micro spheres 8 from becoming lodged in the pores. Next, micro-sphere recovery tests were carried out. The results of these tests are recorded in Table 2.

TABLE 2

Micro-Sphere Recovery from Coaxial Tubular Micro-Sphere Sequestering Device

| Volume to Device, μL | % Recovery | % Std Dev |
|---|---|---|
| 125 | 89 | 5 |
| 150 | 101 | 3 |
| 200 | 91 | 7 |
| 250 | 92 | 5 |
| 300 | 97 | 7 |

Recoveries were good, and reproducibility was satisfactory.

While certain specific embodiments and details have been described to illustrate the present invention, it will be apparent to those skilled in the art that many modifications are possible within the scope of the basic concept of the invention. Other applications are not precluded. For example, another field of application is in the separation of plasma from red blood cells. The red blood cells will not pass through the porous membrane due to their larger size, but the plasma will.

What is claimed is:

1. A sequestering device for micro spheres, the sequestering device comprising:
   a planar porous disk having pores with a size with an appropriate dimension to prevent passage of micro spheres while enabling a liquid carrier in which the micro spheres are suspended to pass through the pores of the disk; and
   a fluidics manifold, constructed and arranged for electronically and automatically controlling operation of the sequestering device, the fluidics manifold including:
   a first multiport selection valve;
   a bi-directional pump, for aspirating a liquid carrier or a suspension of the micro spheres in the liquid carrier;
   a holding coil connecting the first multiport selection valve to the bi-directional pump, for holding the liquid carrier or a suspension of the micro spheres in the liquid carrier;
   a second multiport selection valve;
   an inlet to the porous disk, wherein the inlet is connected to the first multiport selection valve;
   a waste port for the porous disk, the waste port extending from the porous disk to the second multiport selection valve; and
   a flush port from the first multiport selection valve to the porous disk, wherein the inlet to the porous disk and the waste port from the porous disk define first and second passageways, respectively, the first and second passageways are serpentine passageways for causing turbulent flow through the passageways to suspend and keep suspended the micro spheres in the liquid carrier, and the porous disk is disposed between and fluidly connected to the first and second passageways.

2. A method for sequestering micro spheres, the method comprising the steps of:
   (a) aspirating, with a flow cytometer, a suspension of the micro spheres in a liquid carrier;
   (b) using a holding coil to hold the liquid carrier or a suspension of the micro spheres in the liquid carrier;
   (c) loading the holding coil with the suspension of the micro spheres, and with additional liquid carrier for washing the micro spheres and for rinsing the holding coil;
   (d) providing a planar porous disk having pores having a pore size of from about one-tenth to about three-tenths of a micrometer, for retaining the micro spheres within the porous disk while enabling the liquid carrier in which the micro spheres are suspended to pass through the pores of the disk;
   (e) providing the porous disk with an inlet, a waste port, and a flush port, wherein the inlet to the porous disk and the waste port from the porous disk define first and second passageways, respectively, the first and second passageways are serpentine passageways, for causing turbulent flow through the passageways to suspend and keep suspended the micro spheres in the liquid carrier, and the porous disk is disposed between and fluidly connected to the first and second passageways;
   (f) with the waste port open and the flush port closed, transporting the suspension of the micro spheres to the porous disk through the inlet to the porous disk, for retaining the micro spheres in the disk while passing the liquid carrier through the pores of the disk;
   (g) washing the retained micro spheres by flowing the liquid carrier over the retained micro spheres through the inlet to the porous disk to the waste port of the porous disk;
   (h) charging the flush port of the porous disk with the carrier liquid and a bracketing bubble of air;
   (i) with the waste port closed and the flush port open, withdrawing a suspension of the washed micro spheres in the liquid carrier from the porous disk;
   (j) transporting the suspension of the washed micro spheres to the flow cytometer;
   (k) rinsing the holding coil with the liquid carrier; and
   (l) preparing to repeat steps (a) through (k) by dispensing liquid carrier and a bracketing air bubble to the flush port of the porous disk;
the above steps being electronically and automatically controlled by a fluidics manifold which includes first and second multiport selection valves, wherein the inlet and flush port of the porous disk are connected to the first multiport selection valve, and the waste port of the porous disk is connected to the second multiport selection valve.

* * * * *